(12) United States Patent
Xu et al.

(10) Patent No.: US 11,751,591 B2
(45) Date of Patent: Sep. 12, 2023

(54) **STRAIN OF *OCEANOBACILLUS PICTURAE* AND APPLICATIONS THEREOF**

(71) Applicant: Huazhong Agricultural University, Hubei (CN)

(72) Inventors: Xiaoyun Xu, Hubei (CN); Ting Wu, Hubei (CN); Jie Song, Hubei (CN); Siyi Pan, Hubei (CN)

(73) Assignee: Hunzhong Agricultural University, Hubei (CN)

( * ) Notice: Subject to any disclaimer, the term of this patent is extended or adjusted under 35 U.S.C. 154(b) by 291 days.

(21) Appl. No.: 17/013,562

(22) Filed: Sep. 5, 2020

(65) Prior Publication Data
US 2020/0397027 A1 Dec. 24, 2020

(30) Foreign Application Priority Data
Apr. 28, 2020 (CN) .......................... 202010349212.6

(51) Int. Cl.
*A23L 19/20* (2016.01)
*A23L 33/135* (2016.01)
*A23L 5/20* (2016.01)
*C12N 1/20* (2006.01)
*C12R 1/01* (2006.01)

(52) U.S. Cl.
CPC ............... *A23L 19/20* (2016.08); *A23L 5/28* (2016.08); *A23L 33/135* (2016.08); *C12N 1/205* (2021.05); *A23V 2002/00* (2013.01); *C12R 2001/01* (2021.05)

(58) Field of Classification Search
CPC combination set(s) only.
See application file for complete search history.

(56) References Cited

PUBLICATIONS

Lee JS et. al. *Virgibacillus koreensis* sp. nov., a novel bacterium from a salt field, and transfer of Virgibacillus picturae to the genus *Oceanobacillus* as *Oceanobacillus picturae* . . . Int J Syst Evol Microbiol. Jan. 2006;56(Pt 1):251-7. doi: 10.1099/ijs.0.63734-0. PMID: 16403894 (Year: 2006).*

Heyrman, Jeroen et al. (2003). *Virgibacillus carmonensis* sp nov., *Virgibacillus necropolis* sp nov and *Virgibacillus picturae* sp nov. . . . International journal of systematic and evolutionary microbiology. 53. 501-11. 10.1099/ijs.0.02371-0 (Year: 2003).*

* cited by examiner

*Primary Examiner* — Vera Afremova

(57) ABSTRACT

A strain of *Oceanobacillus picturae* and applications thereof are provided, which relate to technical fields of microorganism and food processing. A strain of halophilic bacteria was screened from the brine of Xiangyang Pickled Kohlrabi and was identified as the strain of *Oceanobacillus picturae* by morphology, physical and chemical properties and 16S rRNA sequence. The strain is able to significantly increase the varieties and contents of volatile substances, and decrease the contents of pungent substances in pickled vegetables. The strain of *Oceanobacillus picturae* can improve the taste and the flavor of the pickled vegetables.

1 Claim, 1 Drawing Sheet

Specification includes a Sequence Listing.

SEQUENCE LISTING

<160> NUMBER OF SEQ ID NOS: 1

<210> SEQ ID NO 1
<211> LENGTH: 1392
<212> TYPE: DNA
<213> ORGANISM: Oceanobacillus

<400> SEQUENCE: 1

```
cagaacggaa ctcttcggag ggaagttcgt ggaacgagcg gcggacgggt gagtaacacg      60
taggcaacct gcctgtaaga ctgggataac tcgcggaaac gcgagctaat accggataac     120
actttccatc tcctgatggg aagttgaaag gcggcttttg ctgtcactta cagatgggcc     180
tgcggcgcat tagctagttg gtggggtaac ggctcaccaa ggcgacgatg cgtagccgac     240
ctgagagggt gatcggccac actgggactg agacacggcc cagactccta cgggaggcag     300
cagtagggaa tcttccgcaa tggacgaaag tctgacggag caacgccgcg tgagtgatga     360
aggttttcgg atcgtaaaac tctgttgtcg gggaagaaca agtacgatag taactgatcg     420
taccttgacg gtacccgacc agaaagccac ggctaactac gtgccagcag ccgcggtaat     480
acgtaggtgg caagcgttgt ccggaattat tgggcgtaaa gcgctcgcag gcggttcttt     540
aagtctgatg tgaaatcttg cggctcaacc gtaaacgtgc attggaaact ggaggacttg     600
agtgcagaag aggagagtgg aattccacgt gtagcggtga aatgcgtaga gatgtggagg     660
aacaccagtg gcgaaggcga ctctctggtc tgtaactgac gctgaggagc gaaagcgtgg     720
ggagcgaaca ggattagata ccctggtagt ccacgccgta aacgatgagt gctaggtgtt     780 aggggggtttc cgccccttag tgctgaagtt aacgcattaa gcactccgcc tggggagtac     840
ggccgcaagg ctgaaactca aaagaattga cggggacccg cacaagcggt ggagcatgtg     900
gtttaattcg aagcaacgcg aagaaccttaa ccaggtcttg acatcctttg acacctctag     960
agatagagtt ttccttcgg ggacaaagtg acaggtggtg catggttgtc gtcagctcgt    1020
gtcgtgagat gttgggttaa gtcccgcaac gagcgcaacc cttgatctta gttgccagca    1080
tttagttggg cactataagg tgactgccgg tgacaaaccg gaggaaggtg gggatgacgt    1140
caaatcatca tgccccttat gacctgggct acacacgtgc tacaatggac ggaacaaagg    1200
gaagcgaacc cgcgaggtcc agcaaatccc ataaaaccgt tctcagttcg gattgcaggc    1260
tgcaactcgc ctgcatgaag ccggaatcgc tagtaatcgc ggatcagcat gccgcggtga    1320
atacgttccc gggtcttgta cacaccgccc gtcacaccac gagagttcgt aacacccgaa    1380
gtcgtagagg ta                                                        1392
```

STRAIN OF *OCEANOBACILLUS PICTURAE* AND APPLICATIONS THEREOF

CROSS REFERENCE OF RELATED APPLICATION

The application claims priority under 35 U.S.C. 119(a-d) to CN 202010349212.6, filed Apr. 28, 2020.

BACKGROUND OF THE PRESENT INVENTION

Field of Invention

The present invention relates to technical fields of microorganism and food processing, and more particularly to a strain of *Oceanobacillus picturae* and applications thereof.

Description of Related Arts

Pickled vegetables have a long history with profound historical and cultural heritage in China, which belong to high-salt foods with the salt content reaching 20%. There are a large number of halophilic bacteria in the high-salt foods, which play an important role in the process of food production and storage. Halophiles in the high-salt foods have great influences on the quality of food, especially the color, surface viscosity and flavor. They improve the taste of the product, and are suitable to be used as a microbial starter.

During the production process of soy sauce, the *Tetragenococcus halophilus* species is halophilic lactic acid bacteria exhibiting in the later period of soy sauce mash fermentation. This species is closely related to the ethyl carbamate which is the main flavor substances in the soy sauce (LIAO Danyi et al., Isolation and Arginine Metabolism Detection of a *Tetragenococcus halophilus* strain, Journal of Food Science and Biotechnology, Vol. 35, No. 1, 2016). As a food starter, moderately halophilic eubacteria are popular in the salt fermented food (ZHAO Bai-Suo et al., Biotechnology Applications in Moderately Halophilic Eubacteria, Microbiology China, Vol. 34, No. 2, 2007).

In the prior art, there is no technology about the analysis and identification of halophilic bacteria under high salt concentration of vegetables and their effects on volatile substances. Isolating and identifying the halophilic bacteria in the pickled vegetables, exploring the varieties of halophilic bacteria, and studying the effects of these halophilic bacteria on the volatile substances in the vegetables will help to improve the taste and flavor substance content of the pickled vegetables.

SUMMARY OF THE PRESENT INVENTION

In view of the above problems in the prior art, the present invention provides a strain of *Oceanobacillus picturae* and applications thereof, so as to solve some problems or at least alleviate some problems in the prior art.

Technical solutions of the present invention are described as follows.

A strain of *Oceanobacillus picturae* is provided, which has been deposited in China Center for Type Culture Collection (CCTCC) on Dec. 20, 2019 with a deposit number of CCTCC NO: M 20191070.

Applications of the strain of *Oceanobacillus picturae* in pickled vegetables are provided as follows.

A method for improving a taste of pickled vegetables comprises steps of: inoculating a bacteria solution of a strain of *Oceanobacillus picturae* into brine of the pickled vegetables during a preparation process of the pickled vegetables.

Preferably, an inoculation amount of the bacteria solution into the brine in volume ratio is 6%.

Preferably, the method further comprises a step of: after inoculating, culturing at a constant temperature of 37° C.

Preferably, the pickled vegetables comprise Xiangyang Pickled Kohlrabi.

A method for increasing varieties and/or contents of volatile substances in pickled vegetables comprises steps of: inoculating a bacteria solution of a strain of *Oceanobacillus picturae* into brine of the pickled vegetables during a preparation process of the pickled vegetables.

Preferably, an inoculation amount of the bacteria solution into the brine in volume ratio is 6%.

Preferably, the method further comprises a step of: after inoculating, culturing at a constant temperature of 37° C.

Preferably, the pickled vegetables comprise Xiangyang Pickled Kohlrabi.

A method for decreasing contents of pungent substances in pickled vegetables comprises steps of: inoculating a bacteria solution of a strain of *Oceanobacillus picturae* into brine of the pickled vegetables during a preparation process of the pickled vegetables.

Preferably, an inoculation amount of the bacteria solution into the brine in volume ratio is 6%.

Preferably, the method further comprises a step of: after inoculating, culturing at a constant temperature of 37° C.

Preferably, the pickled vegetables comprise Xiangyang, Pickled Kohlrabi.

Preferably, the pungent substances comprise Allyl isothiocyanate.

The beneficial technical effects of the prevent invention are described as follows.

A strain of halophilic bacteria was screened from the brine of Xiangyang Pickled Kohlrabi and was identified as the strain of *Oceanobacillus picturae* by morphology, physical and chemical properties and 16S rRNA sequence. The strain is able to significantly increase the varieties and contents of volatile substances, and decrease the contents of pungent substances in the pickled vegetables. The strain of *Oceanobacillus picturae* can improve the taste and the flavor of the pickled vegetables.

DETAILED DESCRIPTION OF THE PREFERRED EMBODIMENT

Figure 1:
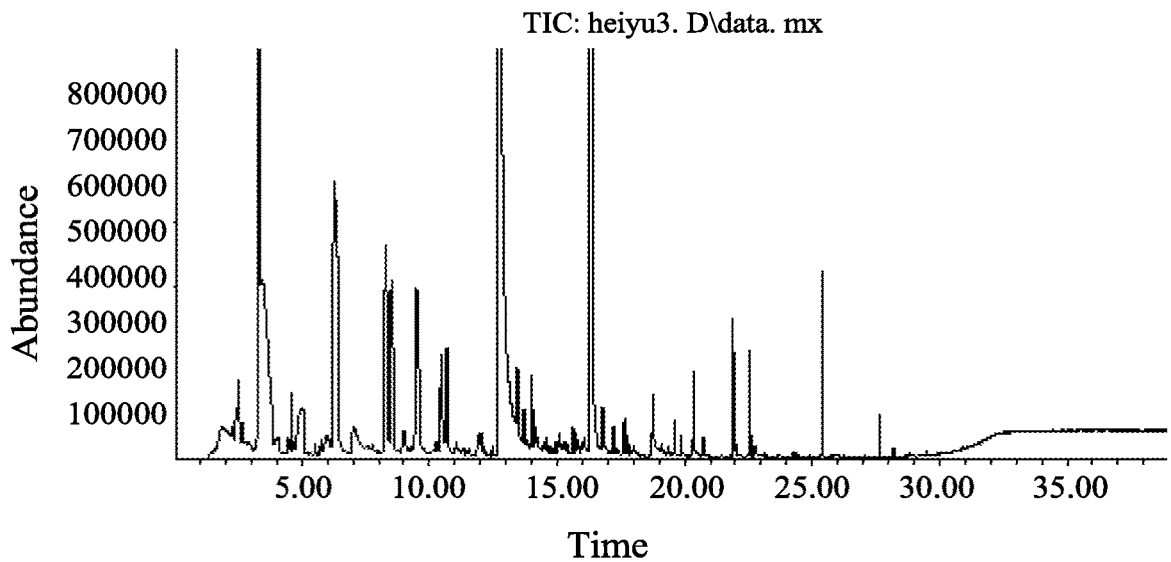
FIG. 1 shows a gas chromatograph of volatile substances in brine of a control group.

In order to make objects, technical solutions and advantages of the present invention clearer, the present invention is further described in detail with examples. The devices and reagents used in the examples are commercially available unless otherwise noted. The examples are only for explaining the present invention, not for limiting the present invention, since various modifications and substitutions can be made without departing from the present invention.

The present invention provides a strain of *Oceanobacillus picturae* and applications thereof. The strain has been deposited in the China Center for Type Culture Collection (CCTCC) on Dec. 20, 2019 with a deposit number of CCTCC NO: M 20191070. The institution (CCTCC) is located in Wuhan University, China, and the strain is named as *Oceanobacillus picturae* G8. The screening methods and applications of the *Oceanobacillus picturae* G8 are described in the following examples.

Example 1 Isolation and Identification of Strain

1. Screening and Identification of Halophilic Bacteria

The brine of Xiangyang Pickled Kohlrabi, 1 mL, as the sample was coated on the solid medium of high salt LB-Agar powders, wherein every 1000 ml of the solid medium contains 10 g tryptone, 5 g yeast extract, 10 g NaCl, and 18 g agar. The plates were placed for culture at a constant temperature of 37° C. Then, colonies were picked and streaked onto corresponding agar plates for obtaining single colonies. As a result, 10 single colonies were obtained. All of the colonies were inoculated into the brine of Xiangyang Pickled Kohlrabi, and a strain was screened out according to the varieties and contents of volatile substances in the brine. Hereinafter, the strain was referred to simply as G-8.

2. Identification of Strain

1) Morphological Characteristics

The G-8 is gram-positive bacteria, whose spore staining was positive with the characteristics of being circular, transparent, convex in the middle and smooth, and having uneven edges on the high salt LB-Agar powders.

2) Physical and Chemical Properties

The G-8 is positive in the glucose test, fructose test and maltose test, and negative in the rhamnose, sucrose, mannose, lactose, sorbitol, mannitol and inositol test, and cannot be determined in the arabinose test. The strain is also positive in the oxidase test, catalase test, V.P test and hydrogen sulfide test, and negative in the amylase, nitrate reduction and nitrite test. The salt tolerance of the G-8 is 20%, and the range of pH is 6.5 to 8.0.

manual injection. Injection port: GC. Mass spectrometer: enabled. Chromatographic conditions: the chromatographic separation was performed using a HP-5 MS 30 m×250 nm×0.25 um column, and helium was used as a carrier gas with a flow rate of 1.2 ML/min; the injection temperature was 250° C. while the initial temperature of the column is 40° C., maintaining for 1 minute; the column temperature was firstly increased to 130° C. with a speed of 5° C./min, then increased to 200° C. with a speed of 8° C./min, and finally increased to 250° C. with a speed of 12° C./min, maintaining for 7 minutes. Mass spectrum conditions: the ion source temperature was 230° C.; the quadrupole temperature was 150° C.; the ionization mode was electron ionization (EI); and the scope of the data to be collected was from 55 m/z to 550 m/z.

Figure 2:
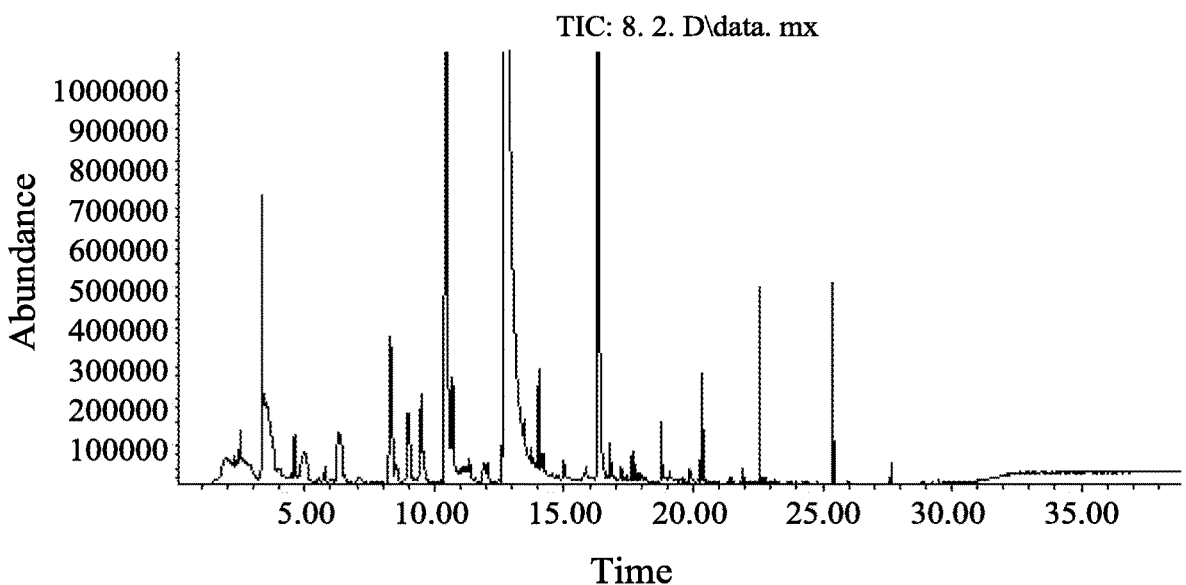
FIG. 2 shows a gas chromatograph of volatile substances in brine which was fermented by *Oceanobacillus picturae* G8.

FIG. 1 and FIG. 2 show gas chromatographs of volatile substances. The varieties and contents of volatile substances in the brine of Xiangyang Pickled Kohlrabi were described as follows.

In the control group, there were 34 varieties of volatile substances, including 1 alkane compound, 1 olefine compound, 0 phenol compound, 1 alcohol compound, 1 acid compound, 3 aldehyde compounds, 0 benzene compound, 5 ester compounds, 7 ketone compounds, 5 ether compounds, 2 cyanogen compounds, 3 amines compounds and 5 heterocyclic compounds.

In the brine which was fermented by the *Oceanobacillus picturae* G8, there were 43 varieties of volatile substances, including 1 alkane compound, 3 olefine compound, 1 phenol compound, 1 alcohol compound, 0 acid compound, 4 aldehyde compounds, 0 benzene compound, 9 ester compounds, 8 ketone compounds, 6 ether compounds, 1 cyanogen compounds, 3 amines compounds and 6 heterocyclic compounds.

The significant analysis of the content of Allyl isothiocyanate in different groups was conducted with SPSS, and the results are shown in the table 1.

TABLE 1

Significant analysis of content of Allyl isothiocyanate

| Compound | Flavor characteristics | Strain | Control group | Experimental group | Prob |
|---|---|---|---|---|---|
| Allyl isothiocyanate | Pungent and spicy | G-8 | 4.19 ± 0.24 | 0.87 ± 0.01 | 0.0330 |

*$P > 0.05$ means "not significant"; $P \leq 0.05$ means "significant".

3) 16s rRNA Sequence of the Strain Refers to SEQ ID NO. 1.

The terms "G-8" and "G8" are used interchangeably and refer to the *Oceanobacillus picturae* G8.

Example 2 Applications of Strain

The activated strain of G-8 was inoculated into the high salt LB liquid medium and cultured in the shaking incubator at 37° C. for one night with a rotational speed of 200 r/min. Then, the bacteria solution was inoculated into the brine of Xiangyang Pickled Kohlrabi with a volume ratio of 6% and cultured at 37° C. for 30 days. After culturing, the varieties and contents of volatile substances in the fermentation solution were detected by solid-phase microextraction (SPME) and gas chromatography mass spectrometry (GC-MS). Meanwhile, the brine with no G-8 was selected as the control group.

GC-MS: Agilent 7890N-5977B, Agilent Technologies Inc. Headspace extraction time: 45 minutes. Injection mode:

The main source of pungent and spicy flavor in the pickled vegetables is Allyl isothiocyanate which was obtained from glucosinolates catalyzed by mustardase in certain circumstances and caused a poor taste of the pickled vegetables. The content of Allyl isothiocyanate in the brine of Xiangyang Pickled Kohlrabi was decreased after the G-8 was added to the brine, and the taste of Pickled Kohlrabi was improved. It can be concluded that the *Oceanobacillus picturae* G8 is suitable to be used as a microbial starter in the pickled vegetables, so as to significantly increase the varieties and contents of volatile substances, decrease the contents of pungent substances and improve the taste.

It is understood that the examples described herein are for illustrative purposes only, not for limiting the present invention. The various modifications, equivalent replacements and improvements made without departing the spirit and principle of the present invention should be all encompassed in the protection scope of the present invention. All publications, patents, and patent applications cited herein are hereby incorporated by reference in their entirety for all purposes.

What is claimed is:

1. A freeze-dried strain of *Oceanobacillus picturae*, which has been deposited in China Center for Type Culture Collection (CCTCC) on Dec. 20, 2019 with a deposit number of CCTCC NO: M 20191070, wherein the strain is prepared by a method of:

coating 1 mL of brine of Xiangyang Pickled Kohlrabi as a sample on a solid medium of high salt LB-Agar powders, wherein every 1000 ml of the solid medium contains 10 g tryptone, 5 g yeast extract, 10 g NaCl, and 18 g agar, culturing at a constant temperature of 37° C., obtaining 10 single colonies by picking and streaking colonies onto corresponding agar plates, inoculating the 10 single colonies into the brine of Xiangyang Pickled Kohlrabi, and screening out the strain according to varieties and contents of volatile substances in the brine.

* * * * *